United States Patent [19]

Leston

[11] 4,394,526

[45] Jul. 19, 1983

[54] PARA-CRESOL HALIDE SALT COMPLEX USEFUL FOR SEPARATING PARA-CRESOL FROM META-CRESOL

[75] Inventor: Gerd Leston, Pittsburgh, Pa.

[73] Assignee: Koppers Company, Inc., Pittsburgh, Pa.

[21] Appl. No.: 191,203

[22] Filed: Sep. 26, 1980

Related U.S. Application Data

[62] Division of Ser. No. 53,438, Jun. 29, 1979, Pat. No. 4,267,389.

[51] Int. Cl.$^3$ .................... C07C 37/68; C07C 37/66
[52] U.S. Cl. .................... 568/716; 568/702; 568/780; 568/751
[58] Field of Search ............... 568/750, 751, 716, 702, 568/780

[56] References Cited

U.S. PATENT DOCUMENTS

| | | | |
|---|---|---|---|
| 1,980,384 | 11/1934 | Comte | 568/750 |
| 2,042,331 | 5/1936 | Carswell | 568/750 |
| 2,366,538 | 1/1945 | Luten et al. | 568/716 |
| 2,835,714 | 5/1958 | Nixon et al. | 568/716 |
| 4,267,389 | 5/1981 | Leston | 568/750 |

FOREIGN PATENT DOCUMENTS 51-988228  3/1976  Japan .................... 568/716

OTHER PUBLICATIONS

Sharpless et al., "Journal Organic Chemistry", vol. 40, No. 9, (1975), pp. 1252–1257.

*Primary Examiner*—Werren B. Lone
*Attorney, Agent, or Firm*—J. Timothy Keane; Daniel J. Long; Herbert J. Zeh, Jr.

[57] ABSTRACT

Para-cresol is separated from a mixture comprising meta-cresol and various other methylated and ethylated phenols by preferentially complexing the para-cresol with one or more anhydrous or dehydrated inorganic salts selected from the group consisting of calcium bromide, lithium bromide, manganese bromide and magnesium chloride. The anhydrous inorganic salt is added to the phenolic mixture in an amount to give a mole ratio of salt to para-cresol in the mixture in the range of about 0.5 mole to one to about 1.5 mole to one. The para-cresol and salt form a complex and the complex is removed from the mixture of methylated and ethylated phenols. Then the complex is decomposed to recover the para-cresol and salt; the recovered salt may be recycled to complex with more para-cresol.

5 Claims, 1 Drawing Figure

PARA-CRESOL HALIDE SALT COMPLEX USEFUL FOR SEPARATING PARA-CRESOL FROM META-CRESOL

CROSS-REFERENCE TO RELATED APPLICATIONS

This is a division of application Ser. No. 53,438, filed June 29, 1979 now U.S. Pat. No. 4,267,389.

This application is related to applications entitled "Process for Obtaining Para-Cresol and Meta-Cresol from a Mixture of Methylated and Ethylated Phenols Containing Meta- and Para-Cresol," Ser. No. 53,532, "Process for Obtaining Para-Cresol and Meta-Cresol from a Mixture of Methylated and Ethylated Phenols Characterized by Urea Clathration of Meta-Cresol)," Ser. No. 53,531, and "Process for Obtaining Para-Cresol and Meta-Cresol from a Mixture of Methylated and Ethylated Phenols Characterized by Selective Complexation with Calcium Bromide and Sodium Acetate," Ser. No. 53,195, all of Gerd Leston, filed on June 29, 1979, which applications are hereby incorporated by reference.

BACKGROUND OF THE INVENTION

The present invention is directed to a process for separating para-cresol from a mixture of methylated and ethylated phenols. More particularly, the process of the present invention is directed to separating para-cresol from a phenolic mixture containing meta-cresol.

Mixtures of phenolic compounds are derived from coal as products of coal carbonization, or as the middle oil from the hydrogenation of coal, or from petroleum as alkali extracts of cracked petroleum distillate. Some of the phenolic compounds in the mixtures derived from these sources have similar physical properties. These similarities in properties make it difficult to separate some of the phenolic compounds from each other. Para-cresol is, in particular, difficult to separate from other phenolic compounds having similar properties. For example, para-cresol is difficult to separate from meta-cresol, since both compounds have similar boiling points, namely, 201.8° C. and 202.8° C., respectively. The similarity of boiling points of these two compounds precludes their separation practically by fractional distillation.

There are several known methods for separating para-cresol and meta-cresol isomers from a mixture containing the isomers, such as a commercial mixture haaving 40–65 percent of meta-cresol. These methods include treatment of a mixture containing meta- and para-cresol isomers with complexing agents such as urea, sodium acetate, oxalic acid or the like and separation of the meta- or para-cresol isomers in an adduct form. Other methods include the formation of a solid complex between a reagent and one cresol isomer. The reagents used include ortho-toluidine, oxalic acid and hexamethylenetetramine. Still other methods for separating meta- and para-cresol isomers involve azeotropic distillation with benzyl alcohol, or selective solvent extraction with methanol-ligroin, or hydrolysis of the sulfonic acid of meta- or para-cresol, or dibutylation followed by distillation and debutylation. Another recently suggested method for separating meta-cresol and para-cresol isomers takes advantage of the different melting points of the compounds and involves subjecting the meta- and para-cresol isomer mixture to crystallization at pressures of not less than about 300 atmospheres. Only a few of the foregoing methods of separation have any commercial potentialities, the process usually employed being the butylation method. A more efficient method is thus desired to obtain high purity para-cresol and high purity meta-cresol from mixtures of methylated and ethylated phenols containing compounds such as ortho-ethyl phenol, xylenol and other methylated and ethylated phenols having similar boiling points to para-cresol and meta-cresol.

An article entitled "Rapid Separation of Organic Mixtures by Formation of Metal Complexes," Journal Organic Chemistry, Volume 40, No. 9, 1975, Sharpless, Chong and Scott, describes a convenient and efficient technique for resolving alcohol mixtures. The technique involves preferential complexing of an alcohol by calcium chloride or manganese chloride, examples of useful alcohols being cis- and trans-4-tert-butylcyclohexanol, geraniol, and cyclohexanol. The article further notes that other alcohols, such as large and hindered alcohols, form complexes very slowly, and that the speed of complex formation can be increased by using a small amount of a lower aliphatic alcohol as a catalyst for complexing.

SUMMARY OF THE INVENTION

It has been found that para-cresol complexes with certain anhydrous or dehydrated inorganic salts, such as calcium bromide, lithium bromide, manganese bromide and magnesium chloride, preferentially over other methylated and ethylated phenolic compounds. This preferential complexing can be used as a means for separating and purifying para-cresol from a mixture of methylated and ethylated phenols that have similar boiling points to para-cresol.

The process of the present invention comprises adding to a mixture of methylated and ethylated phenols containing para-cresol and usually meta-cresol one or more anhydrous inorganic salts selected from the group consisting of calcium bromide, lithium bromide, manganese bromide and magnesium chloride in a mole ratio of anhydrous or dehydrated inorganic salt to para-cresol in the mixture in the range from about 0.5 to one to about 1.5 to one, in the presence of a non-aqueous solvent to produce a complex between the inorganic salt and the para-cresol, whereby the complex formed may be separated from the mixture and then decomposed to yield para-cresol.

Another feature of the present invention is the production of the salt-para-cresol complex in the presence of meta-cresol. This complex can be used to initiate complexing with those anhydrous inorganic salts that are slower in forming complexes with the para-cresol. Also, the complex can be used as a chemical intermediate in producing purified para-cresol.

In the process of the present invention an important variable is the salt to para-cresol mole ratio, and to a lesser extent the variables of para-cresol concentration in the mixture of methylated and ethylated phenols, the solvent used and the temperature of complexing. The salt/para-cresol mole ratio is generally in the range of about 0.5 to one to about 1.5 to one. The para-cresol concentration can be any concentration but generally is at least that concentration that can be purified or separated economically. The solvent must be a non-aqueous solvent, since water will react with the anhydrous inorganic salt to form one or more hydrates. Generally, the non-aqueous solvent should not, itself, complex with the salt or at least not more readily than the para-cresol. The addition of the salt to the mixture of methylated and ethylated phenols can be initially with or without the use of a solvent, but once the salt is added a solvent should then be employed to facilitate the mixing of the salt and mixture. Generally, the temperature of complexing ranges from ambient temperature to a temperature of around 130° C. Higher temperatures are favored when the amount of para-cresol in the mixture is small, that is, around 10 percent by weight. If the complex formation is not initiated at the higher temperatures, then the temperature can be lowered to initiate complex formation and then raised to the higher temperature. If the complex formation is slow, an initiator such as a lower aliphatic alcohol or a previously formed complex of salt and para-cresol can be used.

Once the complex is formed it can be separated from the mixture by any method known to those skilled in the art for separating solid complexes from liquids. Once separated, the complex can be decomposed by therml decomposition at atmospheric pressure, or by distillation at reduced pressure, or by treatment with water, or by treatment with alcohol. After the complex is decomposed, the purified para-cresol is recovered in a second mixture and the anhydrous inorganic salt can be recycled for futher complex formation with para-cresol. It is a feature of the invention that the recovered inorganic salt may be recycled and introduced back into the second mixture containing the previously purified para-cresol and minor amounts of meta-cresol and other methylated and ethylated phenols. The second mixture will thus contain a recomplexation product of para-cresol and salt, which product is then separated and thereafter decomposed to recover the para-cresol and salt. The successively purified para-cresol will then be contained in a third mixture, also containing successively lower amounts of meta-cresol and other phenolic compounds. The para-cresol may thus be treated sequentially with the inorganic salt to provide successive mixtures having higher and higher concentrations of para-cresol and lower amounts of other phenolic compounds.

DETAILED DESCRIPTION OF THE INVENTION

In the process of the present invention para-cresol can be separated or purified from a mixture of methylated and ethylated phenols having similar boiling points to the para-cresol and meta-cresol. The methylated and ethylated phenolic compounds are those methylated and ethylated phenols that do not form complexes with the anhydrous inorganic salts of calcium bromide, lithium bromide, manganese bromide and magnesium chloride or that are not thermodynamically favored over the para-cresol complex or that form complexes at a slower rate than para-cresol. Examples of these methylated and ethylated phenolic compounds include meta-cresol, ortho-cresol, ortho-ethylphenol, 2,4-xylenol, 2,5-xylenol, 2,6-xylenol and trimethylphenols. It is preferred that the mixture contain only para-cresol and meta-cresol, for example, the commercial mixture of meta- and para-cresol containing from 40 to 65 percent of the meta-cresol, the remainder being para-cresol.

It has been found that certain anhydrous or dehydrated inorganic salts when used in a certain mole ratio to the para-cresol in the mixture of methylated and ethylated phenols preferentially complex with the para-cresol. It is believed, but the invention is not limited by this belief, that the para-cresol-salt complex is thermodynamically favored over other complexes formed by methylated and ethylated phenols in the mixture. This belief is based on the fact that even though other alkylated phenols, e.g., meta-cresol, in the mixture form complexes with the above-mentioned anhydrous inorganic salts, the para-cresol complex is the predominant complex formed. A few of the methylated and ethylated phenolic compounds in the mixture, most notably ortho-cresol, do not readily form complexes with the anhydrous or dehydrated inorganic salts. Also, the complexing of para-cresol appears to be thermodynamically controlled whereas the complexing of meta-cresol is kinetically controlled. Although the meta-cresol-salt complex will form first, the para-cresol-salt complex is more thermodynamically stable than the meta-cresol-salt complex. Therefore, given a necessary period of time formation of the para-cresol-salt complex will predominate over the meta-cresol-salt complex.

The amount of para-cresol in the mixture of methylated and ethylated phenols and preferably the mixture of para- and meta-cresol can be practically any amount of para-cresol above about 10 weight percent, since any amount of para-cresol can be separated from the mixture as long as the proper mole ratio of salt to para-cresol is used. The process of the present invention can be used to enrich a mixture containing para-cresol and this enrichment can be done fractionally so as to obtain the maximum enrichment of the mixture in para-cresol. Hereinafter and in the claims of this specification the term "separation" is intended to cover separation, purification and enrichment of para-cresol in mixtures of methylated and/or ethylated phenolic compounds. Generally, it is preferred that the para-cresol be present in the mixture in an amount of at least about 25 weight percent.

In the process of the present invention one or more anhydrous inorganic salts (hereinafter referred to as salt) selected from the group consisting of calcium bromide, lithium bromide, manganese bromide or magnesium chloride is added to the mixture containing para-cresol. The addition is in an amount to give a mole ratio of the salt to the para-cresol in the mixture in the general range of about 0.5 to one to about 1.5 to one. If the mole ratio of salt to para-cresol is above about 1.5 to one, other methylated or ethylated phenolic compounds may complex or may complex to a greater extent and complicate the separation of the para-cresol from the mixture. If the mole ratio of salt to para-cresol is below about 0.5 to one, then the maximum amount of para-cresol present in the mixture will not be separated and the yield of the process would be decreased. The preferred mole ratio of salt to para-cresol depends on the particular salt used. For calcium bromide the preferred mole ratio of salt to para-cresol is about 0.8 to one to about 1.2 to one. The preferred mole ratio of salt to para-cresol for lithium bromide is in the range of about 0.8 to one to about 1.2 to one. For manganese bromide the preferred mole ratio of salt to para-cresol is in the range of about 0.8 to one to about 1.2 to one. The preferred mole ratio of salt to para-cresol for magnesium chloride is in the range of about 0.8 to one to about 1.2 to one. To obtain the mole ratio of salt to para-cresol in the mixture, it is necessary to determine the amount of para-cresol in the mixture of methylated and/or ethylated phenolic compounds. This can be done by any analytical technique known to those skilled in the art for determining the amount of para-cresol in mixtures of organic compounds.

The anhydrous inorganic salts of calcium bromide, lithium bromide, manganese bromide or magnesium chloride that are used in the process and composition of the present invention are the commercial anhydrous salts or the hydrated forms of the salts that have been dehydrated. Dehydration of the salts can be in any manner known to those skilled in the art. Anhydrous salts may be readily prepared from hydrated forms such as aqueous solutions or flaked hydrate forms. It is preferred to heat either the aqueous or flaked form to around 200° C. in air to give the anhydrous material in a solid chunk, which may then be ball milled or ground for use.

The addition of the proper amount of salt can be performed in the presence or absence of a non-aqueous solvent. If the solvent is not present upon the initial addition, it must be added at a later time when upon formation of the complex the mixing of the salt and the mixture becomes difficult. The non-aqueous solvent is added in an amount to facilitate mixing of the components. The non-aqueous solvent should not complex with the salt, or at least it must complex to a lesser extent than the para-cresol. A few examples of non-aqueous solvents that can be used are benzene, toluene, methylene chloride, chlorobenzene, o-dichlorobenzene, and lower aliphatic alicyclic compounds such as hexane as well as oxygenated compounds like ethers, ketones and esters, provided that any complex that is formed with the solvent is weaker than the complex formed with para-cresol. The preferred non-aqueous solvent is toluene because of its low cost.

During the addition of the components and during complexing of the salt and para-cresol-containing mixture, the temperature is in the range of about 20° C. to about 50° C. at atmospheric pressure. If superatmospheric or subatmospheric pressures are employed, the temperature will change accordingly. Increasing the temperature moderately within the range during complexing will increase the rate of complex formation. If the complex is not initiated at the higher temperatures within the above range, the temperature can be lowered to initiate complexing and then raised to increase the rate of complexing. The higher temperatures are preferred when there is a small amount, e.g., around 15 weight percent, of para-cresol in the mixture.

If complex formation with a particular salt is not initiated within a reasonable time, an initiator may be used to catalyze complex formation. Examples of useful initiators include n-aliphatic alcohols such as anhydrous ethanol, anhydrous propanol and anhydrous butanol. A catalytically effective amount of initiator to be used would be around 1 to about 10 weight percent. Alternatively, a useful initiator is a previously formed complex of para-cresol with calcium bromide, lithium bromide, manganese bromide or magnesium chloride. A catalytically effective amount of the complex used may be in the range of about 1 to about 10 weight percent of the mixture being treated. It is preferred to use anhydrous ethanol as a complex initiator or, alternatively, the complex of the same salt used in the complex.

The time taken for complex formation varies for the particular salt used. Lithium bromide is extremely fast in forming the complex with the para-cresol while calcium bromide, magnesium chloride and manganese bromide are somewhat slower. Lithium bromide forms the complex within around 3 to 5 minutes compared with several hours for the other salts. The preferred anhydrous inorganic salt is calcium bromide since it has high selectivity and gives good conversions.

The complex formation of para-cresol and the anhydrous inorganic salt can be performed in any conventional reaction equipment, since the mixture and salt are not very corrosive. Also, complexing can be performed in a batch manner or continuous manner.

Once the para-cresol-salt complex, preferably the para-cresol calcium bromide complex, is formed, the complex is separated from the mixture of methylated and ethylated phenols. This separation can be by any method and in any equipment known to those skilled in the art for separating a solid complex from a liquid solution. Preferably, the complex is separated by filtration or centrifugation to produce a supernatant liquid of methylated and ethylated phenols and a para-cresol-salt complex. The para-cresol-salt complex contains predominantly para-cresol complexed with the salt but may also contain small amounts of meta-cresol and other methylated and ethylated phenols complexed with the salt.

The filtered complex of para-cresol and the salt may be washed with solvent and is then decomposed to release the para-cresol and recover the salt that can be recycled for additional complexing. The decomposition can be performed by heating the complex to the decomposition temperature of about 200° C. at atmospheric pressure or by distilling the complex at a reduced pressure, or by hydrolysis, or by cleavage with other agents like alcohol. Thermal decomposition is the preferred manner for releasing the para-cresol and recovering the salt since it is the most economic method of decomposition. Thermal decomposition can be performed in any equipment known to those skilled in the art to be useful in conducting decomposition reactions. Preferably, the thermal decomposition is performed in a Rinco evaporator at temperatures up to about 200° C. and at atmospheric pressure. Alternately, the complex can be decomposed at a temperature of 125° C. to 175° C. under reduced pressures. An advantage of thermal decomposition over hydrolysis is that an activated form of the salt is thus prepared which can be recycled to complex with para-cresol. Alternatively, the complex can be hydrolyzed with a sufficient amount of water to decompose all of the complex. Also, since alcohols form stronger complexes than phenolic compounds, the alcohols can be used to cleave the complex, the alcohol being substituted in the complex for the para-cresol. A disadvantage of this decomposition method is that the salt is not easily recoverable for recycling.

The recovered para-cresol contained in a second or purified mixture from the decomposition reaction is much purer than the original or first mixture of methylated and ethylated phenolic compounds. The second mixture containing para-cresol may also contain a minor amount of meta-cresol or ortho-ethyl-phenol. If ultimate purity is desired, successive mixtures of para-cresol can be complexed sequentially similar to fractional distillation. The anhydrous inorganic salt recovered after decomposition of the para-cresol-salt complex may be recycled to be added to additional amounts of the mixture of methylated and ethylated phenolic compounds containing para-cresol for additional complexing.

When a mixture of phenolic compounds contains only para-cresol and meta-cresol, the process of the present invention yields a purified para-cresol product and a purified meta-cresol product. The purified meta-cresol product is obtained since it is left behind in the mixture after the para-cresol is complexed and removed. If the mixture of methylated and ethylated phenols contains other methylated and ethylated phenols besides para-cresol and meta-cresol, any method known to those skilled in the art can be used to separate meta-cresol or other methylated or ethylated phenols after para-cresol has been complexed with the anhydrous inorganic salt.

DETAILED DESCRIPTION OF THE DRAWING

Figure 1:
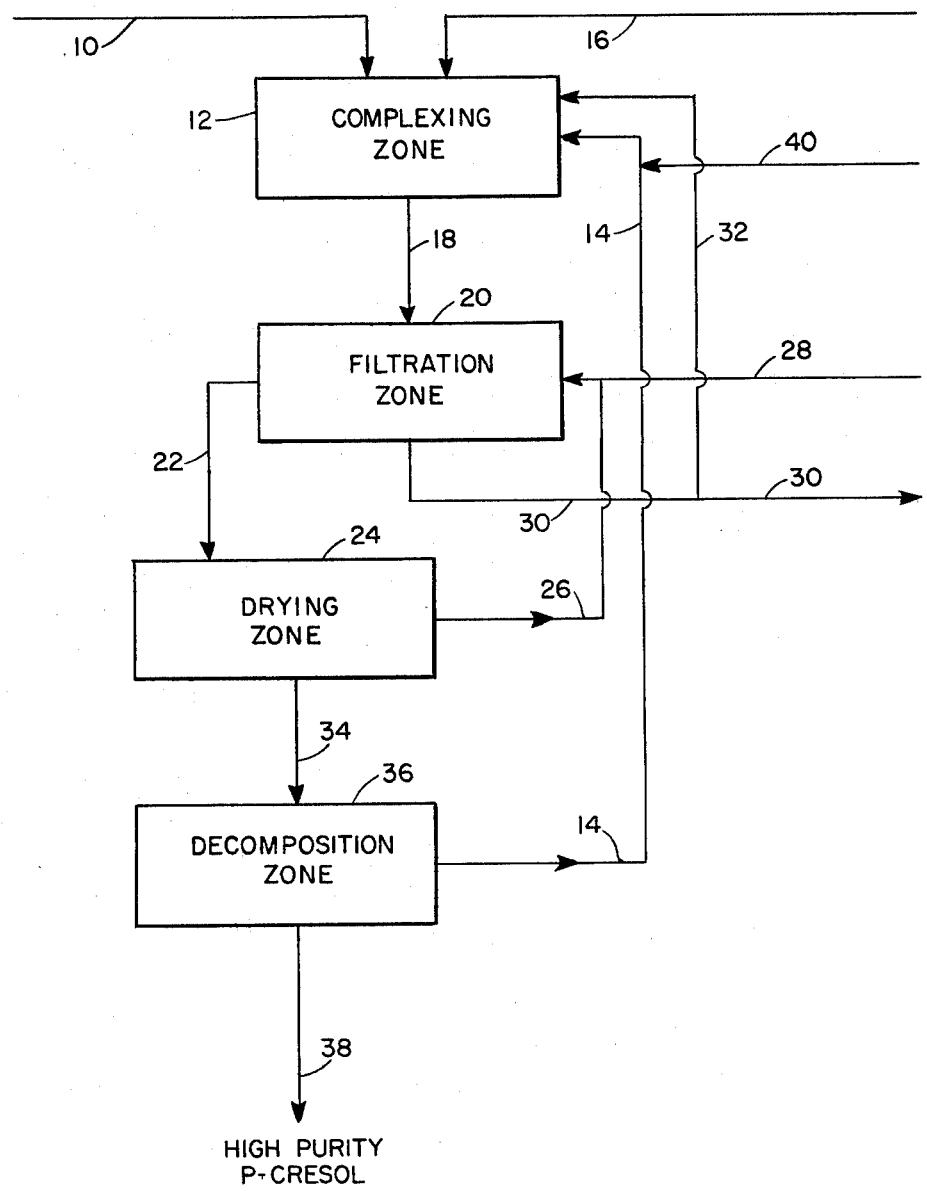
FIG. 1 is a flow diagram of the preferred embodiment of the present invention.

The mixture of methylated and ethylated phenols from which para-cresol is separated may contain meta-cresol and minor amounts of other phenolic compounds. This mixture enters a complexing zone 12 through conduit 10. The preferred anhydrous inorganic salt calcium bromide enters complexing zone 12 through conduit 14. The amount of calcium bromide added to complexing zone 12 is preferably an amount which will give a mole ratio of calcium bromide to para-cresol in the range of about 0.7 to one to about 1.0 to one. A nonaqueous solvent, preferably toluene, is added to complexing zone 12 through conduit 16. In complexing zone 12, meta-cresol, para-cresol, toluene and calcium bromide are mixed at a temperature of around $\phi°$ C. for about eight hours. During this time toluene is present in an amount sufficient for complete mixing of the components during the complexing reaction. At the end of the mixing period, a substantial portion of para-cresol forms a complex with calcium bromide. The complex, along with the supernatant liquid containing meta-cresol, and small quantities of ortho-cresol, xylenol, and ortho-ethylphenol, are removed by conduit 18 from complexing zone 12.

The complex and supernatant liquid are conveyed through conduit 18 to a filtration zone 20, where the complex is separated from the supernatant mixture. The wet complex is conveyed from filtration zone 20 through conduit 22 to a drying zone 24, where the complex is dried and the toluene is separated from the complex. The toluene is then recycled through conduit 26 to conduit 28 where it is added with additional toluene and conveyed to filtration zone 20 to wash the wet complex. The supernatant liquid from which the para-cresol-calcium bromide complex has been removed may be conveyed from filtration zone 20 through conduit 30 and eliminated or may be circulated through conduit 32 back to complexing zone 12 for removal of residual para-cresol.

After the para-cresol-calcium bromide complex has been dried in zone 24, it is conveyed through conduit 34 to decomposition zone 36. In zone 36 the complex is heated to a temperature of around 200° C. at atmospheric pressure to decompose the complex to produce para-cresol and to regenerate the calcium bromide salt. The para-cresol product leaves decomposition zone 36 through conduit 38 and is of a purity of about 98 percent. The regenerated calcium bromide leaves decomposition zone 36 through conduit 14 and is conveyed to complexing zone 12. In an alternative embodiment, additional calcium bromide can be added to conduit 14 through conduit 40 from an outside source.

The following examples set forth specific embodiments of the invention. However, the invention is not to be construed as being limited to these embodiments for there are, of course, numerous possible variations and modifications. All parts and percentages recited in the examples and throughout the specification are by weight, unless otherwise specified.

EXAMPLE I

A reaction vessel equipped with heating means, stirring means and drying means for removing water from the atmosphere in the reaction vessel, is charged with 600 parts calcium bromide, 108 parts meta-cresol, 108 parts para-cresol, 3300 parts hexane and about 3 parts absolute ethanol (saalt to meta-cresol to para-cresol molar ratio being 3 to 1 to 1). The mixture is heated with stirring to a temperature of 25° to 30° C. for about nine hours. After the supernatant hexane solution is withdrawn from the reaction vessel, the solid reaction product is washed with successive amounts of hexane until the wash solution is essentially free of cresols. Water in excess is added to the reaction vessel for hydrolysis of the solid reaction product. Analysis is made on the hydrolyzate and on the supernatant solution at one week, one month and four month intervals. Results are listed in Table I.

EXAMPLE II

A reaction vessel is equipped and charged with components as set forth in Example I, with the exception that the reaction mixture contains a 33 percent increase in the amount of hexane. Reaction procedures are generally as outlined in Example I. Data from analysis of the hydrolyzate and supernatant solution are listed in Table I.

EXAMPLE III

A reaction vessel is equipped and charged with components as set forth in Example I, the molar ratio of the salt, meta-cresol and para-cresol components being 1.5 to 1 to 1. The mixture is heated with stirring to a temperature of 25° to 30° C. for about eight hours. Reaction procedures are generally as outlined in Example I. Data from analysis of the hydrolyzate and supernatant solution are listed in Table I.

EXAMPLE IV

A reaction vessel is equipped and charged with components as set forth in Example I, the molar ratio of calcium bromide, meta-cresol and para-cresol being 1 to 1 to 1. Reaction procedures are generally as in Example I. Data from analysis of the hydrolyzate and supernatant liquid are listed in Table I.

EXAMPLE V

A reaction vessel is equipped and charged with components as set forth in Example I, the molar ratio of calcium bromide, meta-cresol and para-cresol being 0.7 to 1 to 1. The mixture is heated with stirring to a temperature of 25°-30° C. for about 11 hours, reaction procedures otherwise being generally as set forth in Example I. Data from analysis of the hydrolyzate and supernatant liquid are listed in Table I.

EXAMPLE VI

A reaction vessel is equipped and charged with components as set forth in Example V. The mixture is heated with stirring to a temperature of 25°-30° C. for about nine hours, reaction procedures otherwise being generally as set forth in Example I. Data from analysis of the hydrolyzate and supernatant liquid are listed in Table I.

EXAMPLE VII

A reaction vessel is equipped and charged with components as set forth in Example V, with a ten-fold scale-up in component amounts. The mixture is heated with stirring to a temperature of 25°–30° C. for about nine hours. After the supernatant hexane solution is withdrawn from the reaction vessel, the solid reaction product is washed with successive amounts of hexane until the wash solution is essentially free of cresols. Ethanol in 50 percent molar excess to the solid complex of cresol and salt is added to the reaction vessel holding the solid reaction product. Sufficient hexane is added to the reaction vessel for dissolving the cresol isomers displaced by the ethanol from the solid complex. The solid complex is washed successively with hexane and thereafter the combined hexane solutions, together with the salt-ethanol complex, are refluxed. The hexane and ethanol from an azeotrope which is distilled from the solid state, the distillate carrying with it the para-cresol isomer. The solid salt, which is dried under reduced pressure, comprises calcium bromide. Data from analysis of the hydrolyzate and supernatant liquid are listed in Table I.

TABLE I

Calcium Bromide Complexes

| | | Product | | | |
|---|---|---|---|---|---|
| | | Hydrolyzate | | Supernatant Solution | |
| Example | Feed (Mole Ratio) CaBr$_2$/m-cresol/p-cresol | % m-cresol | % p-cresol | % m-cresol | % p-cresol |
| I | 3/1/1 | 41.7$^a$ | 58.3$^a$ | 95.5$^a$ | 4.5$^a$ |
| | | 43.9$^b$ | 56.1$^b$ | 100$^b$ | |
| | | 43$^c$ | 57$^c$ | 94.6$^c$ | 5.4$^c$ |
| II | 3/1/1 | 48$^c$ | 52$^c$ | 93.5$^c$ | 6.5$^c$ |
| III | 1.5/1/1 | 38.9 | 61.1 | 91.6 | 8.4 |
| IV | 1/1/1 | 7 | 93 | 88 | 12 |
| V | 0.7/1/1 | | 100 | 71 | 29 |
| VI | 0.7/1/1 | | 100 | 66 | 34 |
| VII | 0.7/1/1 | | 100 | 65 | 35 |

$^a$Analysis made on one-week-old sample.
$^b$Analysis made on one-month-old sample.
$^c$Analysis made on four-month-old sample.

EXAMPLE VIII

A reaction vessel equipped as in Example I is charged with magnesium chloride, meta-cresol and para-cresol in the molar ratio of 1.5 to 1 to 1, with hexane and ethanol being added in the proportions as set forth in Example I. The mixture is heated to 25°–30° C. with stirring for about 10 hours, other reaction procedures being generally as set forth in Example I. Data from analysis of the hydrolyzate and supernatant solution are set forth in Table II.

EXAMPLE IX

A reaction vessel is equipped and charged with components as in Example VIII, with the exception that the magnesium salt, meta-cresol and para-cresol are in molar ratio of 1 to 1 to 1. Reaction procedures are generally as set forth in Example VIII. Data from analysis of the hydrolyzate and the supernatant liquid are set forth in Table II.

EXAMPLE X

A reaction vessel is equipped and charged with components as in Example VIII. The mixture is heated to 25°–30° C. with stirring for about nine hours, other reaction procedures being generally as set forth in Example VIII. Data from analysis of the hydrolyzate and supernatant solution are set forth in Table II.

EXAMPLE XI

A reaction vessel is equipped and charged with components as set forth in Example VIII, the magnesium chloride, meta-cresol and para-cresol being in a molar ratio of 0.75 to 1 to 1. The mixture is heated to 25°–30° C. with stirring for about nine hours, other reaction procedures being generally as set forth in Example VIII. Data from analysis of the hydrolyzate and supernatant solution are set forth in Table II.

EXAMPLE XII

A reaction vessel is equipped and charged with components as set forth in Example VIII, the magnesium chloride, meta-cresol and para-cresol being in a molar ratio of 0.5 to 1 to 1. The mixture is heated to 25°–30° C. with stirring for about 11 hours, other reaction procedures being generally as set forth in Example VIII. Data from analysis of the hydrolyzate and supernatant solution are set forth in Table II.

EXAMPLE XIII

A reaction vessel is equipped and charged with components as set forth in Example XII. The mixture is heated to about 50° C. with stirring for about 13 hours. After the supernatant hexane solution is withdrawn from the reaction vessel, the solid reaction product is washed with successive amounts of hexane until the wash solution is essentially free of cresols. The solid complex is heated at 200° C. at atmospheric pressure for four hours, then at about 0.2 atmosphere for two hours, at about 0.13 atmosphere for one hour and at about 0.07 atmosphere for one hour. A portion of the dried solid complex is added as a "seed" crystal to a mixture of magnesium chloride, meta-cresol and para-cresol in a molar ratio of 0.5 to 1 to 1 in hexane. After eight hours there is observed a 14 percent decrease in cresol concentration in the supernatant liquid. The supernatant hexane solution is withdrawn from the reaction vessel and the solid complex is washed with successive amounts of hexane. Water in excess is added to the solid products for hydrolysis of the complex. Data from analysis of the hydrolyzate and the supernatant solution are set forth in Table II.

TABLE II

Magnesium Chloride Complexes

| | | Product | | | |
|---|---|---|---|---|---|
| | Feed (Mole Ratio) | Hydrolyzate | | Supernatant Solution | |
| Example | MgCl$_2$/m-cresol/p-cresol | % m-cresol | % p-cresol | % m-cresol | % p-cresol |
| VIII | 1.5/1/1 | 31.5 | 68.5 | 67.7 | 32.3 |
| IX | 1/1/1 | 8.3 | 91.7 | 75.1 | 24.8 |
| X | 1.5/1/1 | 46.2 | 53.8 | 64.5 | 35.5 |
| XI | 0.75/1/1 | 11.5 | 88.5 | 66.6 | 33.4 |
| XII | 0.5/1/1 | 11.5 | 88.5 | 66.6 | 33.4 |
| XIII | 0.75/1/1 | 27 | 73 | 62.3 | 37.7 |

Although specific examples of the instant invention have been set forth hereinabove, it is not intended that the invention be limited solely thereto, but is to include all the variations and modifications falling within the scope of the appended claims.

What is claimed is:

1. A complex between para-cresol and an anhydrous or dehydrated inorganic halide salt selected from the group consisting of calcium bromide, magnesium chloride, lithium bromide and manganese bromide, said complex formed in the presence of meta-cresol and a non-aqueous solvent.

2. The complex of claim 1 wherein said halide salt is calcium bromide.

3. The complex of claim 1 wherein said non-aqueous solvent is toluene.

4. The complex of claim 1 wherein said complex is formed in the presence of a complexing initiator.

5. The complex of claim 4 wherein said complexing initiator is ethanol.

* * * * *